United States Patent [19]

Tauber et al.

[11] 4,437,838
[45] Mar. 20, 1984

[54] APPARATUS FOR PREPARING EXAMINATIONS

[75] Inventors: Robert T. Tauber; Randolph T. Tauber, both of Erie, Pa.

[73] Assignee: TTK Communication Products, Erie, Pa.

[21] Appl. No.: 371,736

[22] Filed: Apr. 26, 1982

[51] Int. Cl.³ ............................................. G09B 1/10
[52] U.S. Cl. ................................ 434/363; 282/29 B; 354/292
[58] Field of Search ....................... 434/363, 354, 353; 282/29 B; 354/292

[56] References Cited

U.S. PATENT DOCUMENTS

| | | | |
|---|---|---|---|
| 3,003,502 | 10/1961 | Zalkind | 282/29 B X |
| 3,264,967 | 8/1966 | Wood | 354/292 |
| 3,724,103 | 4/1973 | Walker | 434/354 |

FOREIGN PATENT DOCUMENTS 918410 10/1946 France ............................... 282/29 B Primary Examiner—William H. Grieb
Attorney, Agent, or Firm—Ralph Hammar

[57] ABSTRACT

Each examination question is individually typed on a standard sized card having uniformly spaced holes along the left-hand margin. The cards are stored in a pool or bank or file from which the questions for the examination are selected by any desired procedure. The selected cards are attached to a card aligner having upstanding pins of the same uniform spacing as the holes in the cards. The cards are arranged on the aligner shingle fashion with the question on each card exposed and with the remainder of each card covered by the card containing the following question.

When assembled, the assembly of cards may be photocopied and reproduced by conventional means.

2 Claims, 4 Drawing Figures

APPARATUS FOR PREPARING EXAMINATIONS

In the traditional procedure for preparing examinations, questions are selected from a bank or pool of questions accumulated from various sources such as questions suggested by book publishers, questions used in previous years, questions suggested by current teaching personnel, etc. After selection, questions are typed, proofread, revised, corrected, and then duplicated by photocopying or other procedure. Sometimes the revisions are slight, but frequently revisions may involve rewriting, deletion, and substitution. All of this involves considerable secretarial work.

This invention is intended to minimize the secretarial work involved in the preparation of examinations. According to this invention, each question is typed in a standard format on the front face of a standard size card which is large enough to carry the longest question with space for answers. The questions are accumulated in a bank from various sources such as textbook publishers, prior examinations, the current teaching staff, etc., and the questions for each examination are selected from the bank and assembled in order with the text of the questions properly spaced. The assembly is then photocopied and reproduced in conventional manner. Before reproduction, changes may be made by removing and replacing cards, and even by typing new cards for new questions or for old questions requiring revision. However, because the typing and proofreading is confined to one typing of one card for each question, much of which can be done in spare time throughout the year, this invention eliminates about 90% of the time required by the traditional procedure without degrading the appearance of the examination.

Figures 1, 2, 3, 4:
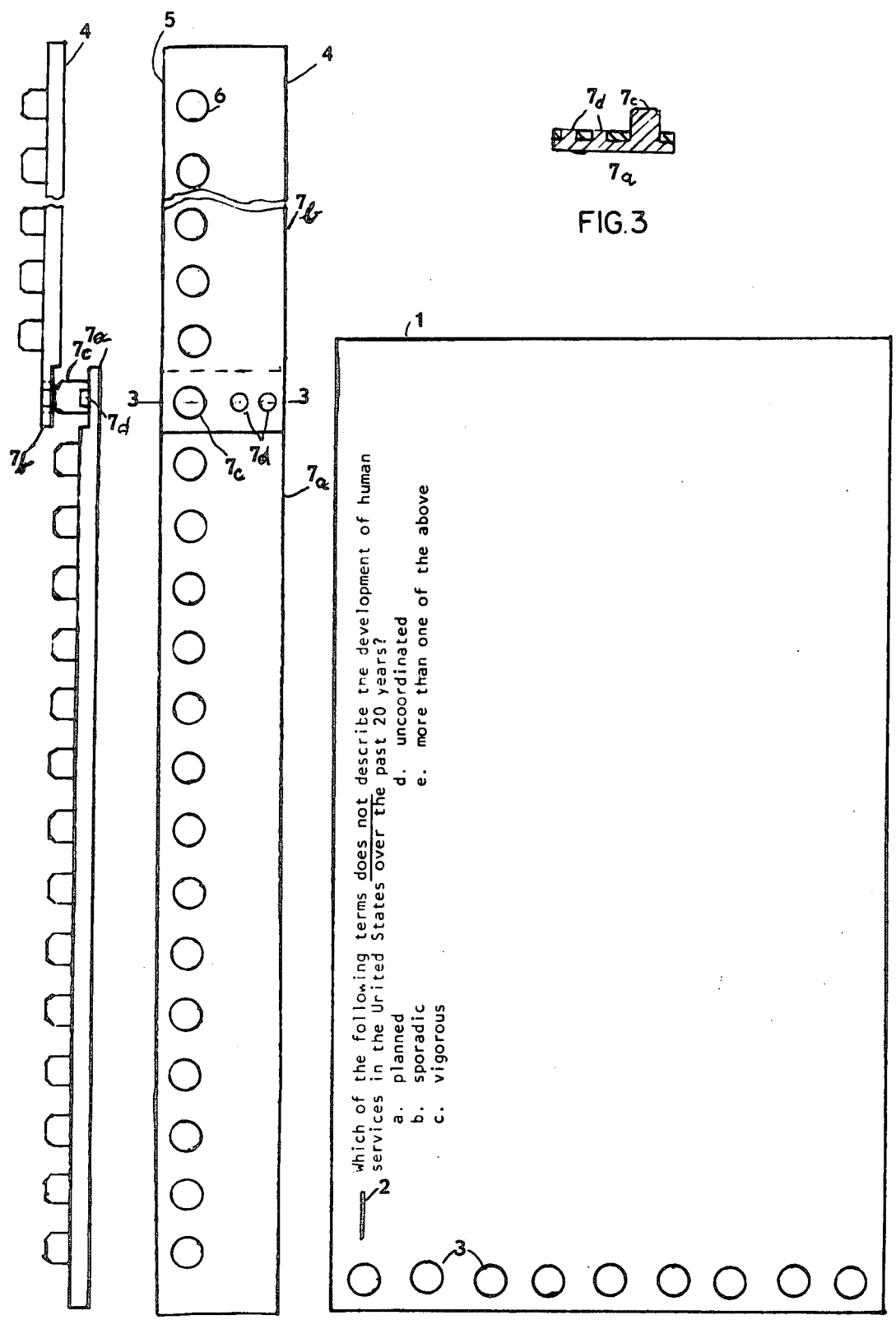
FIG. 1 is a plan view of a card aligner.
FIG. 2 is an edge view of the card aligner of FIG. 1 with the joint between the parts of the aligner separated.
FIG. 3 is a section on line 3—3 of FIG. 1.
FIG. 4 is a view of the front face of a card carrying an examination question.

The apparatus preferably uses standard size cards 1 such as 5"×8" which permits complete interchangeability of the cards and also permits the use of standard paper sizes for the completed examination, such as from 8 to 8½" by 10 to 14". On the front face of each card in the upper left-hand corner is a single line 2 of reproducing ink which has three purposes. First, it marks the upper line of the examination question. Second, the right-hand end of the line marks the left-hand margin for the typed question. Third, the line 2 provides a space in which a question number may be inserted.

Along the left-hand margin of the card is a series of holes 3 of uniform size and spacing, such as quarter inch holes on half inch centers. The purpose of these holes is to provide positive alignment of the cards when pressed onto a series of pins of size sufficiently smaller so as to permit easy insertion and removal and yet provide a good friction grip for the cards. The front face of the cards may also contain other information in non-reproducing ink. The back side of the card may contain instructions to the typist for typing the examination question on the card, instructions for assembling the cards for an examination, identification of the course and textbook, instructions for grading the answers to the question, and records of the student response to the question. The material on the reverse side of the card can be of non-reproducing ink, although this may not be necessary if the card is sufficiently opaque. The cards are large enough to handle any type of question, essay, multiple choice, true or false, etc., and to provide space for the question and answer. In the case of true or false or multiple choice questions, the possible answers will be typed below the question with space left for the student to indicate which is the correct answer. For the essay type question, space will be left below the question in which the answer can be written.

The holder and aligner for the cards is a strip 4 about an inch wide and slightly longer than the longest sheet of paper to be used for the examination. In the particular structure shown, which was for use with paper up to 14" in length, the strip 4 was 15" long. Along the left-hand side 5 of the strip and spaced on the same spacing as the holes 3 in the cards are upstanding pins 6. If the strip 4 were made of wood, the pins 6 could be dowel pins. For the particular construction shown where the strip 4 is made of injection molded plastic, the pins are ¼" in diameter and on ½" centers. The pins are accurately spaced so that when a card is placed over the pins 6, its left-hand edge is flush with the left-hand edge of the aligner strip 4.

For the purpose of facilitating shipping and storage, the aligner strip 4 is made in two parts with a lap joint 7a, 7b at the center. The joint part 7a has a quarter inch pin 7c of the same height as the remaining pins 6 and two smaller pins 7d whose upper ends are substantially flush with the upper surface of the strip 4. The joint part 7b has holes complementary to the pins 7c, 7d so that when the joint is assembled, the structure behaves as though made of a single piece of plastic. For shipping and storing, the joint 7a, 7b can be broken and the two parts of the aligner will then be of slightly less length than the width of the cards. This permits shipping and storage of the aligner in the same box as the cards.

For any particular examination, the questions are selected from a bank or file containing question cards indexed for the course or particular subject matter to be examined. After selection of the questions, the cards are arranged in the desired order and the left-hand margin of the card containing the first question is placed over the pins at the top of the left-hand side of the card aligner. The same process is followed by the succeeding questions with the cards being arranged in shingle fashion with the upper end of the second card overlapping the lower end of the first card, etc.

For multiple choice and true-false questions, the cards are placed as close together as possible so long as the typing on a card already in place is not blocked out by the card being placed on the card aligner. For short answer and essay questions, leave as much space as needed for the students' answers before adding the next card. For questions incorporating a chart, diagram, etc., place the diagram on a card first, then follow it with questions about the chart or diagram on separate cards. Instead of charts of diagrams, sketches, paste-ups or pictures may be used with the same procedure.

When the card holder is loaded to capacity, place the card holder and cards face down on a copying machine and obtain a master copy. This copy will contain the text material of the individual cards, the index lines 2 of the individual cards, and will have the spacing between the individual questions which has been allotted for the students' answers. If the spacing is sufficient and the arrangement of the questions appears satisfactory, then each question should be numbered, the number being placed directly above the index line 2.

Depending upon the length of the examination, more than one card holder may be needed for the cards and the complete examination may result in more than one page.

When all of the questions have been numbered, it is still possible to review the complete examination and to make changes by removing one or more cards and substituting new cards containing substitute questions. At most, this will involve retyping substitute cards and renumbering questions on new master copies.

We claim:

1. Equipment for preparing an examination of a plurality of questions comprising a plurality of rectangular cards each carrying a single question and with space for non-reproducing administrative information such as instructions for grading answers and records of student response to the question, said cards being of uniform size having along the left-hand margin a vertical row of a plurality of uniformly spaced holes and an index mark of reproducible ink indicating the top line and the left-hand margin of the question, and a card holder comprising a strip of length equal to or greater than the length of the page on which the examination questions are to be assembled, said strip having a left-hand margin underlying and covered by the left-hand margin of the cards and a plurality of uniformly spaced pins registering with and frictionally gripping the holes in the cards, the cards being laid single fashion on the strip with the holes over the pins and with the question on each card exposed and with the remainder of the card covered by the card containing the following question, whereby a photocopy of the cards assembled on the card holder after placing on the photocopy the reproducible number for each question on its index mark provides a master copy of a page of examination questions which may be reproduced to provide multiple copies.

2. The structure of claim 1 in which the left-hand margin of the strip registers with the left-hand margin of the cards.

* * * * *